US010537229B2

(12) United States Patent
Okamoto

(10) Patent No.: US 10,537,229 B2
(45) Date of Patent: Jan. 21, 2020

(54) INTRODUCTION DEVICE

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/042,537

(22) Filed: Feb. 12, 2016

(65) Prior Publication Data

US 2016/0157699 A1 Jun. 9, 2016

Related U.S. Application Data

(63) Continuation of application No. PCT/JP2014/075684, filed on Sep. 26, 2014.

(30) Foreign Application Priority Data

Oct. 2, 2013 (JP) .................................. 2013-207681

(51) Int. Cl.
*A61B 1/00* (2006.01)
*A61B 1/005* (2006.01)
*G02B 23/24* (2006.01)

(52) U.S. Cl.
CPC ........ *A61B 1/0052* (2013.01); *G02B 23/2476* (2013.01)

(58) Field of Classification Search
CPC ........ A61B 1/0052; A61B 2017/00318; A61B 1/00066

(Continued)

(56) References Cited

U.S. PATENT DOCUMENTS 5,733,245 A 3/1998 Kawano
6,638,213 B2 * 10/2003 Ogura .................. A61B 1/0051
600/146

(Continued)

FOREIGN PATENT DOCUMENTS

JP S63-043637 A 2/1988
JP H09-168507 A 6/1997

(Continued)

OTHER PUBLICATIONS

English translation of International Preliminary Report on Patentability dated Apr. 14, 2016 together with the Written Opinion received in related International Application No. PCT/JP2014/075684.

(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An introduction device includes an operation main body, a bending section capable of bending in a first direction and a second direction, a first rotary body configured to be operated at a time of bending the bending section in the first direction, and a second rotary body configured to be operated at a time of bending the bending section in the second direction, the second rotary body being configured such that a part of an outer edge is located on an extension plane which is defined by extending the first surface, or the part of the outer edge is located more on the distal-end direction side of the first shaft portion than the extension plane.

4 Claims, 11 Drawing Sheets

(58) Field of Classification Search
USPC .................................................. 600/146, 148
See application file for complete search history.

(56) References Cited

U.S. PATENT DOCUMENTS

| | | | | |
|---|---|---|---|---|
| 2009/0030273 A1* | 1/2009 | Murakami | ............ | A61B 1/0052 |
| | | | | 600/106 |
| 2009/0281388 A1* | 11/2009 | Ito | ...................... | A61B 1/00073 |
| | | | | 600/121 |
| 2012/0302829 A1 | 11/2012 | Omoto | | |
| 2013/0057667 A1* | 3/2013 | McGrath | ............ | A61B 1/00052 |
| | | | | 348/65 |
| 2013/0201309 A1 | 8/2013 | Takahashi | | |
| 2014/0012087 A1* | 1/2014 | Omoto | ............... | G02B 23/2476 |
| | | | | 600/146 |
| 2014/0135580 A1 | 5/2014 | Omoto et al. | | |

FOREIGN PATENT DOCUMENTS

| | | | |
|---|---|---|---|
| JP | 2004-008342 A | | 1/2004 |
| JP | WO-2013/129416 | * | 9/2013 |
| WO | WO 2012/074013 A1 | | 6/2012 |
| WO | WO 2013/015003 A1 | | 1/2013 |
| WO | WO 2013/129494 A1 | | 9/2013 |

OTHER PUBLICATIONS

International Search Report dated Dec. 9, 2014 issued in PCT/JP2014/075684.
Japanese Office Action dated Jul. 14, 2015 issued in JP 2015-522314.

* cited by examiner

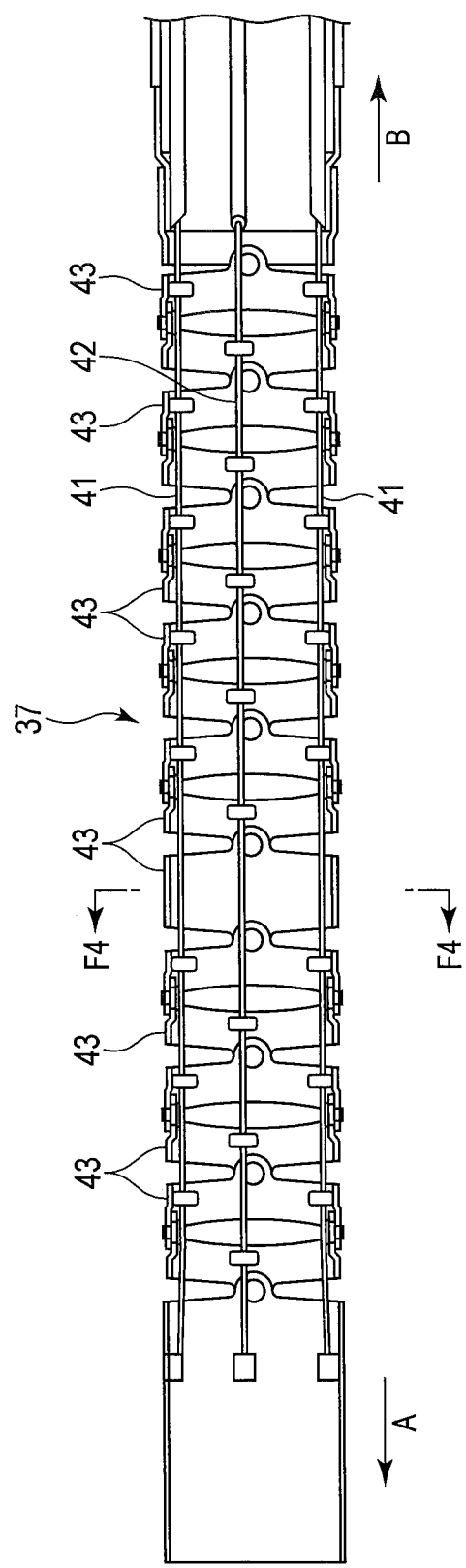
F I G. 3

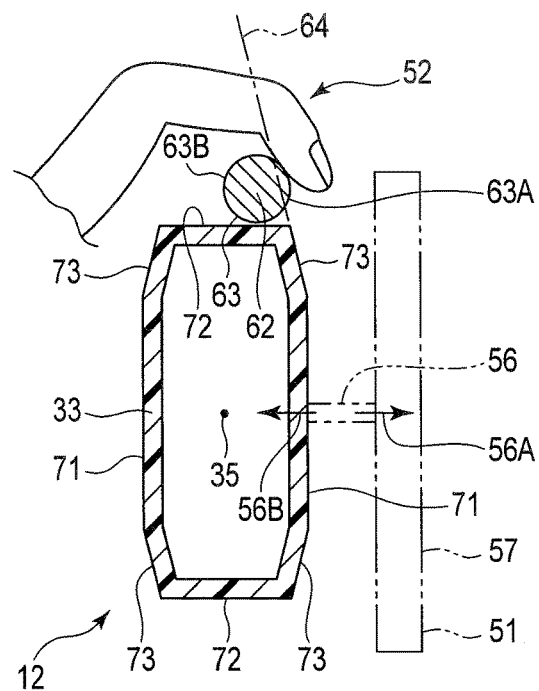
F I G. 14
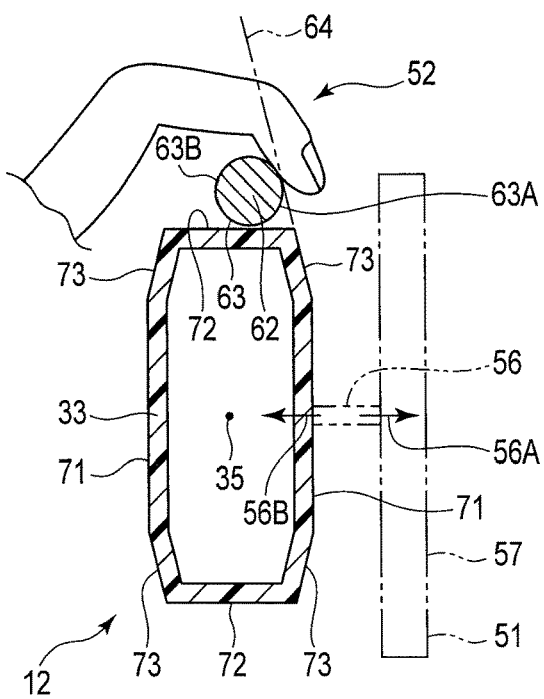
F I G. 15

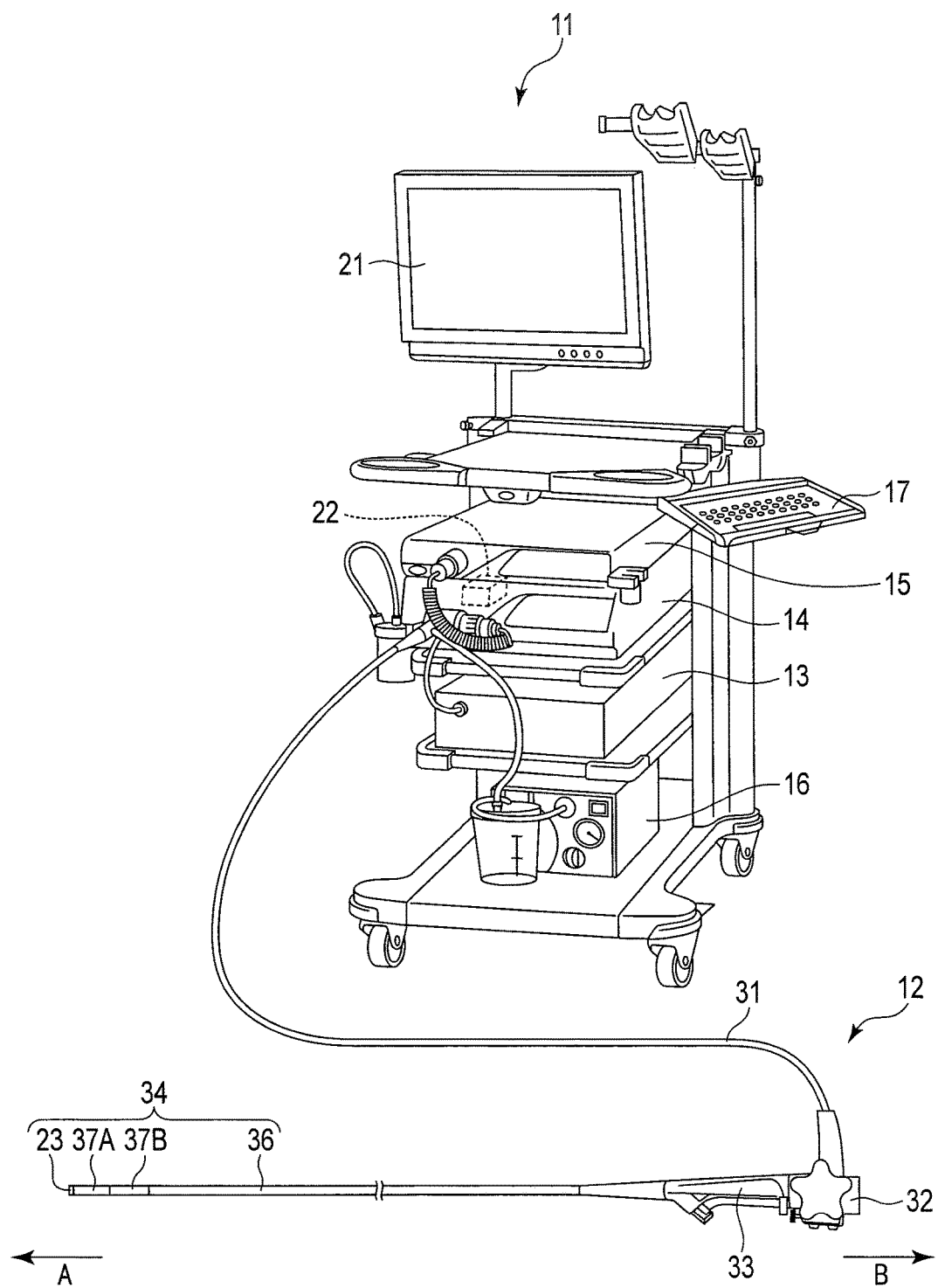
F I G. 18

INTRODUCTION DEVICE

CROSS-REFERENCE TO RELATED APPLICATIONS

This application is a Continuation Application of PCT Application No. PCT/JP2014/075684, filed Sep. 26, 2014 and based upon and claiming the benefit of priority from prior Japanese Patent Application No. 2013-207681, filed Oct. 2, 2013, the entire contents of all of which are incorporated herein by reference.

BACKGROUND OF THE INVENTION

1. Field of the Invention

The present invention relates to an introduction device which is inserted into a cavity.

2. Description of the Related Art

In general, an introduction device for introduction into a cavity, such as an endoscope, includes, for example, an insertion section with flexibility which is inserted into a subject in order to observe, treat, etc. a diseased part in the subject; and an operation section for performing an operation for bending the insertion section in a UD direction and an RL direction. The operation section includes a UD angle knob for performing an operation in the UD direction, and an RL angle knob for performing an operation in the RL direction. When a diseased part is observed, treated, etc., the UD angle knob and RL angle knob are operated, and thus the insertion section can be bent in the UD direction and RL direction.

In addition, there is an endoscope in which the bending of a bending section in the UD direction and RL direction is driven by a motor.

For example, in an endoscope of PCT International Publication No. 2012-074013, bending of the insertion section in the up-and-down (UD) direction is performed by a manual operation, and bending in the right-and-left (RL) direction is automatically operated by driving of a motor. The operation section includes a knob for an operation in the up-and-down (UD) direction, and a dial for an operation in the right-and-left (RL) direction.

BRIEF SUMMARY OF THE INVENTION

In order to achieve the object, an introduction device according to one embodiment of the invention includes an operation main body provided with a first surface; a grip section neighboring the operation main body and provided along a longitudinal axis; a bending section capable of bending in a first direction and a second direction crossing the first direction; a first rotary body configured to be rotatable about a first shaft portion projecting from the first surface, and to be operated at a time of bending the bending section in the first direction; and a second rotary body configured to be rotatable about a second shaft portion projecting from the operation main body, and to be operated at a time of bending the bending section in the second direction, the second rotary body being configured such that a part of an outer edge, which part is located on a distal-end direction side of the first shaft portion, is located on an extension plane which is defined by extending the first surface, or the part of the outer edge, which part is located on the distal-end direction side of the first shaft portion, is located more on the distal-end direction side of the first shaft portion than the extension plane, and configured such that a part of the outer edge, which part is located on a proximal-end direction side of the first shaft portion, is located more on the proximal-end direction side of the first shaft portion than the extension plane.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional view illustrating bend pieces, first wires and second wires, which are disposed within a bending section of the endoscope device shown in FIG. 1.

FIG. 14 is a cross-sectional view illustrating the position of the second rotary body, FIG. 14 being a cross-sectional view in which an endoscope of an endoscope device of a third embodiment is cut along a plane perpendicular to the longitudinal axis.

FIG. 15 is a cross-sectional view illustrating the position of the second rotary body, FIG. 15 being a cross-sectional view in which an endoscope of an endoscope device of a fourth embodiment is cut along a plane perpendicular to the longitudinal axis.

FIG. 18 is a perspective view illustrating an endoscope device of a modification of the first to sixth embodiments.

DESCRIPTION OF EMBODIMENTS

First Embodiment

Figure 1:
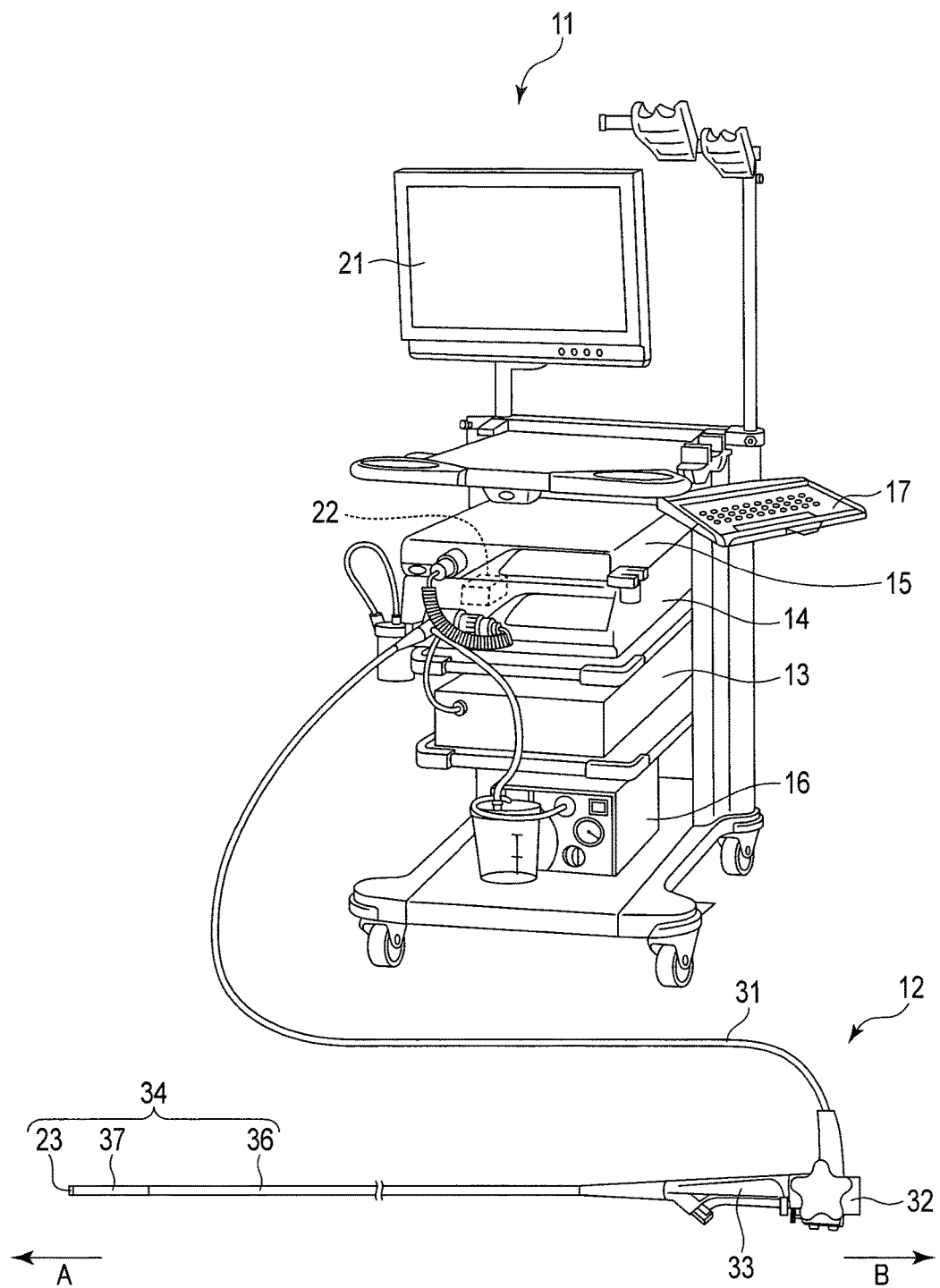
FIG. 1 is a perspective view illustrating the entire structure of an endoscope device of a first embodiment.

FIG. 1 illustrates the entire structure of an endoscope device of the present invention. As illustrated in FIG. 1, an endoscope device 11 includes an endoscope 12, a control device 13, a light source device 14, an image capturing device 15, an air-feed/water-feed/suction device 16, a keyboard 17, a monitor 21, and an actuator unit 22.

The light source device 14 supplies, under the control of the control device 13, light to illumination lenses 24 disposed at a distal rigid section 23 (to be described later) of the endoscope 12. The air-feed/water-feed/suction device 16 feeds, under the control of the control device 13, air/water to a nozzle 25 disposed at the distal rigid section 23 of the endoscope 12, and sucks a liquid or tissue from a living body via the nozzle 25. The image capturing device 15 processes, under the control of the control device 13, an image of a subject, which was captured through an objective lens 26 at the distal rigid section 23 of the endoscope 12, and displays the processed image on the monitor 21.

The control device 13 is connected to a rotation detection sensor 49 which is built in an operation main body 32 (to be described later) of the endoscope 12. The rotation detection sensor 49 detects a rotational direction and a rotation amount of a second rotary body 52, and transmits a detection signal to the control device 13 (see FIG. 7). The control device 13 operates the actuator unit 22 in accordance with the rotation amount detected by the rotation detection sensor 49, and bends the bending section 37 in an R direction or L direction.

The actuator unit 22 can apply a driving force so as to bend the bending section 37 (to be described later) of the endoscope 12 in the R direction and L direction in an XZ plane. The actuator unit 22 is composed of, for example, a motor such as a servo motor.

As illustrated in FIG. 1, the endoscope 12 includes a universal cord 31, an operation main body 32, a grip section 33 which neighbors the operation main body 32, and an insertion section 34 which extends from the grip section 33 and is inserted in a cavity (subject). The endoscope 12 is an example of the introduction device.

The endoscope 12 is connected to the control device 13, light source device 14, image capturing device 15 and air-feed/water-feed/suction device 16 via the universal cord 31. A flexible shaft (not shown) is passed through the universal cord 31. The driving force of the actuator unit 22 is transmitted via the flexible shaft and a gear and a pulley, which are provided within the operation main body 32, to a pair of second wires 42 which are wound around this pulley.

Figure 5:
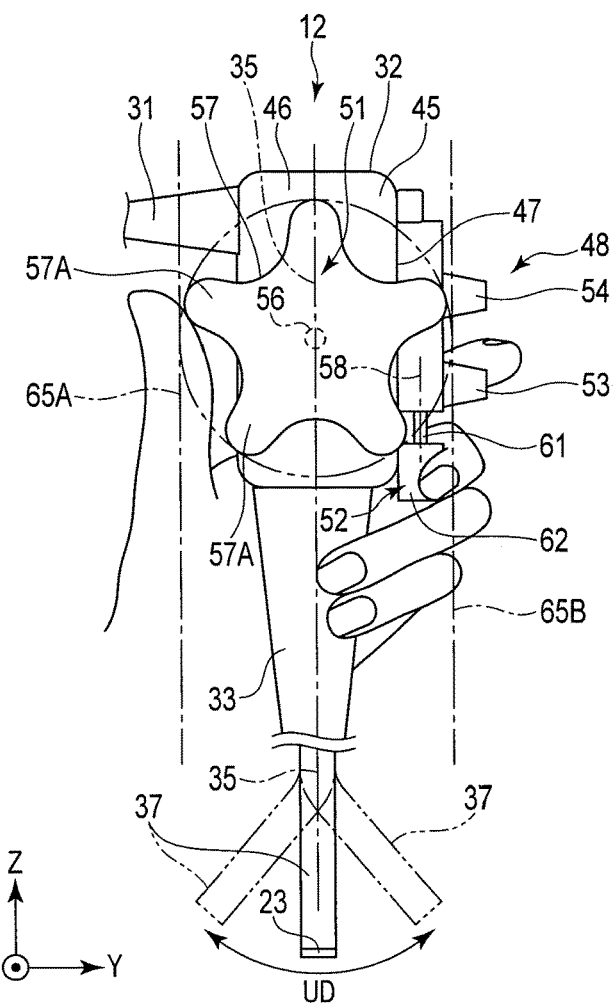
FIG. 5 is a front view illustrating, from a first surface side (front-surface side), an operation main body of the endoscope device shown in FIG. 1.

The insertion section 34 is provided along a longitudinal axis 35 (see FIG. 1, FIG. 5, etc.). Incidentally, as illustrated in FIG. 5, a direction that is parallel to the longitudinal axis 35 is defined as a Z axis. In FIG. 1, arrow A indicates a distal-end direction of the longitudinal axis 35, and arrow B indicates a proximal-end direction of the longitudinal axis 35. The insertion section 34 includes a flexible section 36 which is long and narrow and has flexibility, a bending section 37 provided at a distal end of this flexible section 36, and a distal rigid section 23 provided at a distal end of this bending section 37.

Figure 4:
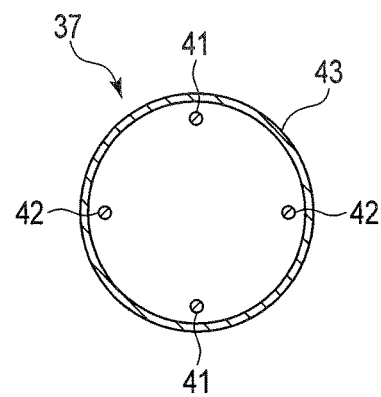
FIG. 4 is a cross-sectional view taken along line F4-F4 in FIG. 3.

As illustrated in FIG. 3 and FIG. 4, a pair of first wires 41 for bending the bending section 37 in the U direction and D direction and a pair of second wires 42 for bending the bending section 37 in the R direction and L direction are passed through the inside of the flexible section 36 and bending section 37. The bending section 37 includes a plurality of bend pieces 43 which are arranged along the longitudinal axis 35 of the insertion section 34.

Figure 2:
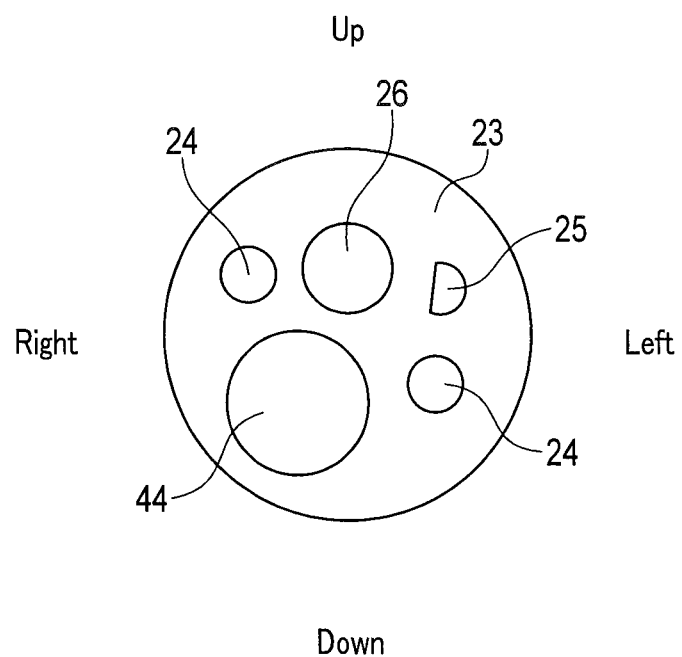
FIG. 2 is a front view illustrating, from an end face side, a distal rigid section of the endoscope device shown in FIG. 1.

As illustrated in FIG. 2, the distal rigid section 23 is provided with an objective lens 26, a treatment instrument insertion channel 44, illumination lenses 24, and a nozzle 25 which is capable of supplying water and air for cleaning the distal end face of the distal rigid section 23, and sucking a liquid or tissue in the living body.

Figure 6:
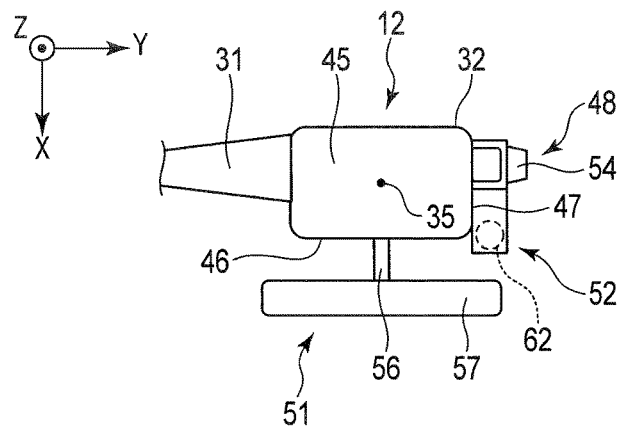
FIG. 6 is a side view illustrating, from a proximal-end direction, the operation main body of the endoscope device shown in FIG. 5.

As illustrated in FIG. 5 and FIG. 6, the operation main body 32 includes a case 45 which is formed of, e.g. a synthetic resin material so as to have an inside space; a first rotary body 51 which is provided on a first surface 46 side of the case 45; a second rotary body 52 which is provided on a second surface 47 side of the case 45; a button section 48 which is provided on the second surface 47 side of the case 45; and a rotation detection sensor 49 (see FIG. 7) which is provided within the case 45.

The case 45 includes a first surface 46, and a second surface 47 which is provided at a position neighboring the first surface 46. The first surface 46 extends in a direction crossing a first shaft portion 56 of the first rotary body 51 which will be described later. The second surface 47 extends in a direction crossing (perpendicular to) the first surface 46 from an outer edge portion of the first surface 46. It can be said, in other words, that the second surface 47 extends from the outer edge portion of the first surface 46 along a direction in which the first shaft portion 56 of the first rotary body 51 (to be described later) extends. Each of the first surface 46 and second surface 47 may be a flat surface or a curved surface. When the first surface 46 and second surface 47 are curved surfaces, it is preferable that these surfaces are formed in a manner to bulge to the outside relative to the longitudinal axis 35. O-rings are interposed between the first shaft portion 56 and case 45 and between the second shaft portion 61 and case 45, thereby keeping water-tight the inside of the case.

The rotation detection sensor 49 is composed of, for example, a potentiometer. However, another kind of sensor (e.g. a rotary encoder) may be used if the sensor can detect the rotation amount of the second shaft portion 61. The rotation detection sensor 49 reads the rotational angle of the second dial portion 62 via the second shaft portion 61 of the second rotary body 52, and detects the rotational direction and rotation amount of the second dial portion 62.

Figure 7:
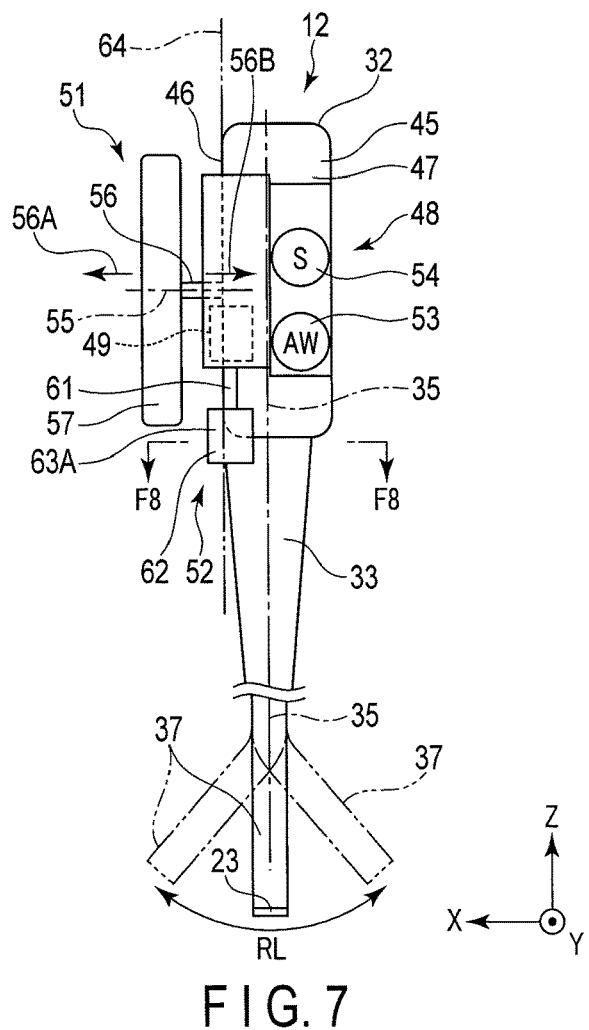
FIG. 7 is a side view illustrating, from a second surface side (side-surface side), the operation main body of the endoscope device shown in FIG. 5.

As illustrated in FIG. 5 and FIG. 7, the button section 48 includes a first button 53 (air-feed/water-feed button, AW) for feeding air and water to the distal rigid section 23 of the endoscope 12 via the nozzle 25, and a second button 54

(suction button, S) for sucking at the distal rigid section 23 of the endoscope via the nozzle 25.

The first rotary body 51 is a so-called UD knob which is operated to bend the bending section 37 at a time of bending the bending section 37 in a U direction and a D direction, that is, at a time of bending the bending section 37 in two directions. If a user rotates the first rotary body 51 about a center axis (first center axis 55) by a finger or the like, the bending section 37 is bent in accordance with the rotation amount in the U direction or D direction (these directions are comprehensively referred to as "first direction") in a YZ plane shown in FIG. 5.

The first rotary body 51 includes a first shaft portion 56 (first shaft) which projects from the first surface 46 of the case 45 of the operation main body 32 and is provided rotatable relative to the case 45; a first dial portion 57 which is fixed to a distal end portion of the first shaft portion 56 and is rotatable about the first shaft portion 56; and a first pulley (not shown) which is provided within the case 45 and is fixed to a proximal end portion of the first shaft portion 56. The first dial portion 57 has a substantially star-like shape, and includes, for example, five claws 57A. The first wires 41 for bending the bending section 37 in the U direction and D direction are wound around the first pulley.

In the endoscope device 11 of the present embodiment, there is no mechanism for bending the bending section 37 in the U direction and D direction by electric driving of a motor or the like. However, like the bending in the R direction and L direction to be described later, the bending section 37 may be bent in the U direction and D direction by electric driving by providing the actuator unit 22 such as a motor. In addition, it is preferable that the first center axis 55 of the first rotary body 51 is formed to cross the longitudinal axis 35 (for example, to be perpendicular to the longitudinal axis 35).

The second rotary body 52 is a so-called RL dial which is operated to bend the bending section 37 at a time of bending the bending section 37 in an R direction and an L direction, that is, at a time of bending the bending section 37 in two directions. If the user rotates the second rotary body 52 about a center axis (second center axis 58), the actuator unit 22 is driven, and the bending section 37 is bent by the driving force of the actuator unit 22. In accordance with the rotation amount of the second rotary body 52, the bending section 37 is bent in the R direction and L direction (these directions are comprehensively referred to as "second direction") in an XZ plane shown in FIG. 7.

For example, if the second rotary body 52 is rotated clockwise by 1.5 rotations (540° rotation), the bending section 37 bends over 180° in the R direction and is set in a maximum bending state in the R direction. Similarly, if the second rotary body 52 is rotated counterclockwise by 1.5 rotations (540° rotation), the bending section 37 bends over 180° in the L direction and is set in a maximum bending state in the L direction.

In the endoscope device 11 of the present embodiment, the angle of actual bending of the bending section 37 is set to be smaller than the rotational angle which is set by the operation input to the second rotary body 52. Thus, in the endoscope device 11 of this embodiment, the rotational angle of the second rotary body 52 (the distance of rotational feed by the finger), which is necessary for bending the bending section 37 by a desired angle, is relatively large. This setting is useful in order to move the bending section 37 in the cavity (living body) by a small angle.

In the meantime, in the present embodiment, although the description was given of the example in which the bending section 37 is bent by electric driving with respect to the R direction and L direction, it is possible to adopt such a configuration that the bending section 37 is manually bent in the R direction and L direction, like the bending mechanism for bending the bending section 37 in the U direction and D direction.

As illustrated in FIG. 5 and FIG. 7, the second rotary body 52 includes a second shaft portion 61 (second shaft) which projects from the operation main body 32 and is rotatable relative to the case 45; and a second dial portion 62 which is fixed to a distal end portion of the second shaft portion 61. The second rotary body 52 is provided on the second surface 47 side. The second dial portion 62 has a columnar shape. The second dial portion 62 has a smaller diameter than the first dial portion 57. The peripheral surface of the second dial portion 62 is provided with, for example, knurling-like recess and projections. A proximal end portion of the second shaft portion 61 is connected to the rotation detection sensor 49 in the inside of the case. In this embodiment, the second rotary body 52 (second dial portion 62) is provided to be exposed from the operation main body 32, and no part of the second dial portion 62 is hidden in the case 45.

Figure 8:
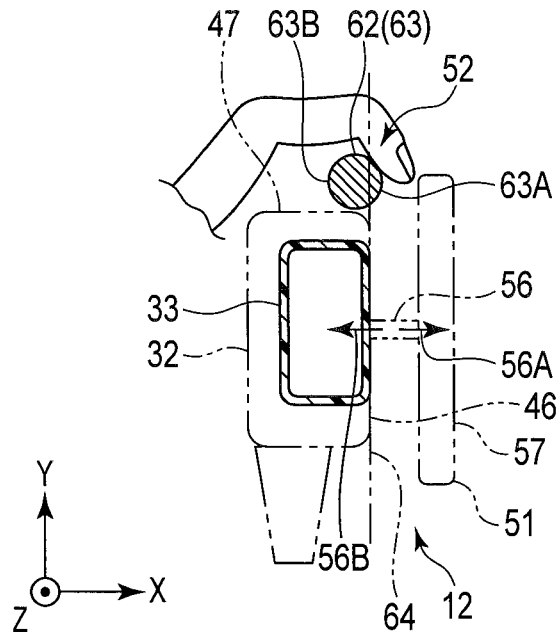
FIG. 8 is a cross-sectional view, taken along line F8-F8 in FIG. 7, illustrating an endoscope of the endoscope device shown in FIG. 7.

As illustrated in FIG. 7 and FIG. 8, in the present embodiment, a part 63A of a circular outer edge 63 of the second rotary body 52 (second dial portion 62), which part 63A is located on the distal-end direction 56A side of the first shaft portion 56, is located more on the distal-end direction 56A side of the first shaft portion 56 than an extension plane 64 which is defined by extending the first surface 46 of the operation main body 32 toward the periphery. In addition, a part 63B of the circular outer edge 63 of the second rotary body 52 (second dial portion 62), which part 63B is located on the proximal-end direction 56B side of the first shaft portion 56, is located more on the proximal-end direction 56B side of the first shaft portion 56 than the extension plane 64.

As illustrated in FIG. 7, the second shaft portion 61 of the second rotary body 52 is, in the direction of extension of the first shaft portion 56, located more on the side (longitudinal axis 35 side) where the operation main body 32 is located, than the extension plane 64. In other words, it can be said that the second shaft portion 61 of the second rotary body 52 is, in the direction of extension of the first shaft portion 56, provided within the range of the thickness dimension of the operation main body 32.

FIG. 5 illustrates, for the purpose of description of the position of the second rotary body 52, two tangents which are in contact with a circumscribed circle of the first rotary body 51 and are parallel to the longitudinal axis 35. One tangent 65A is located on the side where the first rotary body 51 is operated by the thumb, and the other tangent 65B is located on the side opposite to the side where the first rotary body 51 is operated by the thumb. As illustrated in FIG. 5, in the present embodiment, the second shaft portion 61, as viewed from the first surface 46 side, is located between the longitudinal axis 35 and the tangent 65B which is located on the side opposite to the side where the first rotary body 51 is operated by the thumb.

Next, the operation of the endoscope device of this embodiment is described. A doctor, who is a user, holds the operation main body 32 by the left hand. As illustrated in FIG. 5, etc., the universal cord 31 is placed at a position between the left thumb and index finger, the inside of the thumb is placed on the claw 57A of the first dial portion 57, and the grip section 33 is supported by the ring finger and little finger. In addition, the inside of the left index finger is disposed at such a position as to able to operate the first button 53 (air-feed/water-feed button) and second button 54 (suction button), and the inside of the middle finger is placed on the second rotary body 52. Besides, by holding the insertion section 34 by the right hand and inserting the insertion section 34 into a cavity, a desired examination or treatment is performed.

When the doctor wishes to bend the bending section 37 in one of the U direction and D direction (first direction) in the YZ plane, the doctor rotates the first dial portion 57 clockwise or counterclockwise by, for example, the inside of the thumb of the left hand. Thereby, the first pulley, which is fixed to the first shaft portion 56 in the inside of the operation main body 32, rotates, and one of the paired first wires 41, which are wound around the first pulley, is pulled toward the proximal end side of the operation main body 32. Thus, the bending section 37 is bent in either the U direction or D direction. Specifically, if the first rotary body 51 is rotated clockwise in FIG. 5, the bending section 37 bends in the D (downward) direction. If the first rotary body 51 is rotated counterclockwise, the bending section 37 bends in the U (upward) direction.

At this time, for example, after the first dial portion 57 was rotated by a degree (about 72°) corresponding to one claw 57A, if the first dial portion 57 is to be further rotated in the same direction by a degree (about 72°) corresponding to one claw 57A, the left middle finger, for instance, may auxiliary be used. Thereby, the doctor can prevent the bending angle of the bending section 37 from decreasing due to the tension of the pulled first wire 41. This operation is called an assisting operation, and the doctor can temporarily hold the first rotary body 51 so as to stop the rotation of the first rotary body 51 by making use of the fingertip of the left middle finger. In the present embodiment, since the second rotary body 52 is disposed near the first rotary body 51, the assisting operation can naturally be performed by the left middle finger which operates the second rotary body 52.

Figure 9:
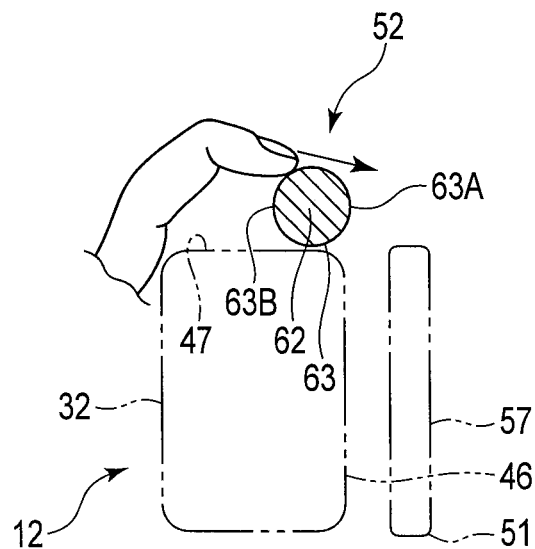
FIG. 9 is a cross-sectional view illustrating the position of a left middle finger before movement at a time when a second rotary body of the endoscope shown in FIG. 8 is rotated clockwise.
Figure 10:
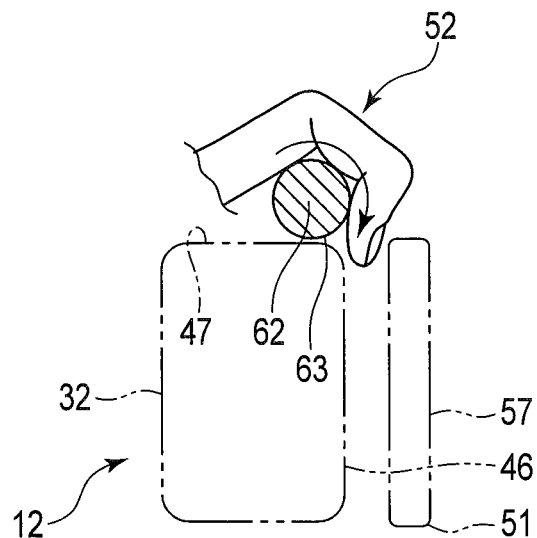
FIG. 10 is a cross-sectional view illustrating the position of the left middle finger after movement at a time when the second rotary body of the endoscope shown in FIG. 9 is rotated clockwise.
Figure 11:
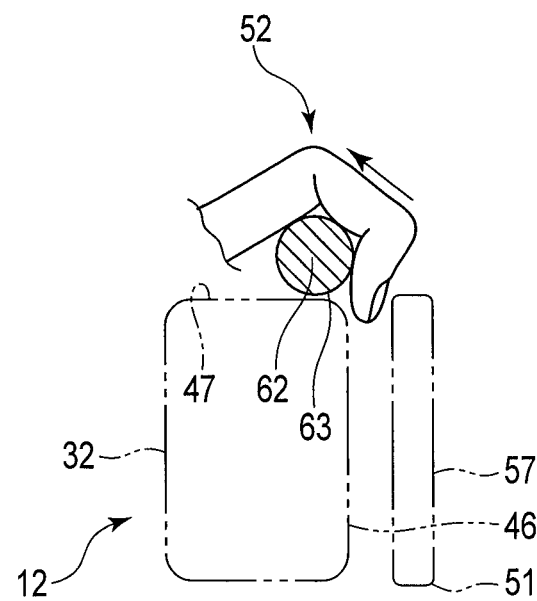
FIG. 11 is a cross-sectional view illustrating the position of the left middle finger before movement at a time when the second rotary body of the endoscope shown in FIG. 8 is rotated counterclockwise.
Figure 12:
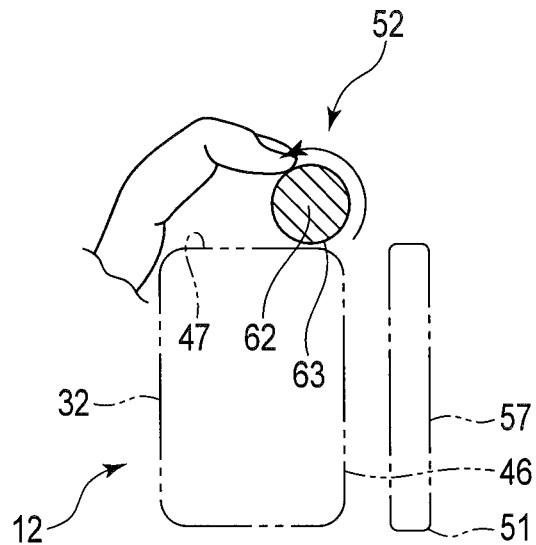
FIG. 12 is a cross-sectional view illustrating the position of the left middle finger after movement at a time when the second rotary body of the endoscope shown in FIG. 8 is rotated counterclockwise.

On the other hand, when the doctor wishes to bend the bending section 37 in one of the R direction and L direction in the XZ plane, the doctor rotates, as illustrated in FIG. 8, etc., the second dial portion 62 clockwise or counterclockwise by the inside of a finger other than the thumb (e.g., left middle finger). As illustrated in FIG. 9 and FIG. 10, if the second dial portion 62 is rotated clockwise, the bending section 37 bends in the R (right) direction. As illustrated in FIG. 11 and FIG. 12, if the second dial portion 62 is rotated counterclockwise, the bending section 37 bends in the L (left) direction.

In the present embodiment, that part 63A of the outer edge 63 of the second rotary body 52, which is located on the distal-end direction 56A side of the first shaft portion 56, is located more on the distal-end direction 56A side of the first shaft portion 56 than the extension plane 64. Thus, when the second rotary body 52 is operated, the finger does not come in contact with the case 45 of the operation main body 32. As illustrated in FIG. 10 and FIG. 11, in each of the cases of clockwise and counterclockwise operations, the length, over which the finger (middle finger) is hooked on the outer edge 63 of the second rotary body 52, can be increased. Thereby, the second rotary body 52 can be rotated over a large angle by a one-time operation.

The rotation detection sensor 49 transmits an electric signal, which corresponds to the rotation amount of the second rotary body 52, to the control device 13. The control device 13 operates the actuator unit 22, and the actuator unit 22 transmits a torque (rotational force) to the paired second wires 42 via the flexible shaft, gear and second pulley. One of the second wires 42 is pulled toward the proximal end side of the operation main body 32, and the bending section 37 bends in either the R direction or L direction.

According to the first embodiment, the introduction device includes the operation main body 32 provided with the first surface 46; the grip section 33 neighboring the operation main body 32 and provided along the longitudinal axis 35; the bending section 37 capable of bending in the first direction and the second direction crossing the first direction; the first rotary body 51 configured to be rotatable about the first shaft portion 56 projecting from the first surface 46, and to be operated at the time of bending the bending section 37 in the first direction; and the second rotary body 52 configured to be rotatable about the second shaft portion 61 projecting from the operation main body 32, and to be operated at the time of bending the bending section 37 in the second direction, the second rotary body 52 being configured such that the part 63A of the outer edge 63, which is located on the distal-end direction 56A side of the first shaft portion 56, is located more on the distal-end direction 56A side of the first shaft portion 56 than the extension plane 64, and the part 63A of the outer edge 63, which is located on the proximal-end direction side 56B of the first shaft portion 56, is located more on the proximal-end direction 56B side of the first shaft portion 56 than the extension plane 64.

According to this structure, the outer edge 63 of the second rotary body 52 can be disposed in a manner to project to the distal-end direction 56A side of the first shaft portion 56. Thereby, when the second rotary body 52 is operated, the finger can be brought to the first surface 46 side. Thus, when the second rotary body 52 is operated, the finger is prevented from abutting on the operation main body 32, and the angle, over which the second rotary body 52 can be rotated by a one-time operation, can be increased. Thereby, the operability of the introduction device can be improved.

In addition, the second rotary body 52 is provided to be exposed from the operation main body 32. Thus, the length, over which the finger is hooked on the second rotary body 52, can be increased, and the operability of the second rotary body 52 can further be enhanced.

Furthermore, the second shaft portion 61 is, in the direction of extension of the first shaft portion 56, located more on the side where the operation main body 32 is located, than the extension plane 64. According to this structure, it is possible to prevent excessive projection of the outer edge 63 of the second rotary body 52 to the distal-end direction 56A side of the first shaft portion 56, which causes difficulty in hooking the finger, leading only to deterioration in operability. Thus, the second rotary body 52 can be disposed within a proper range.

The second shaft portion 61, as viewed from the first surface 46 side, is located between the longitudinal axis 35 and the tangent 65B which is located on the side opposite to the side where the first rotary body 51 is operated by the thumb, the tangent 65B being one of the tangents which are in contact with the circumscribed circle of the first rotary body 51 and are parallel to the longitudinal axis 35. According to this structure, the second rotary body 52 can be disposed near the first rotary body 51. Thereby, the assisting operation for holding the first rotary body 51 can naturally be performed by utilizing the left middle finger which operates the second rotary body 52, and the operability of the introduction device can be improved.

Second Embodiment

Figure 13:
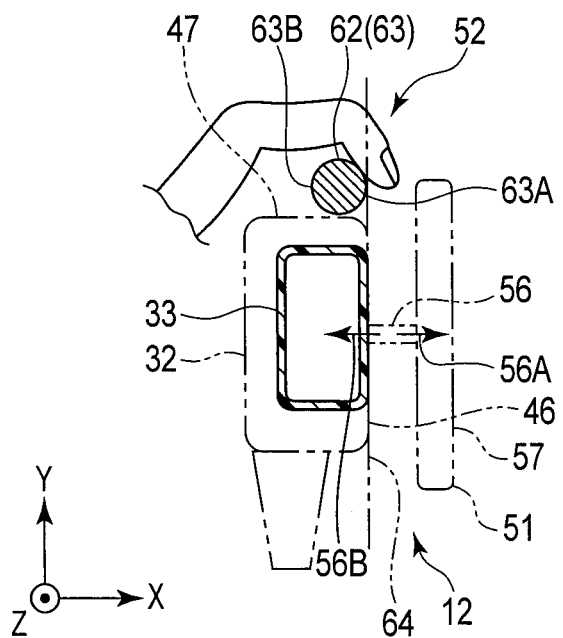
FIG. 13 is a cross-sectional view illustrating the position of the second rotary body, FIG. 13 being a cross-sectional view in which an endoscope of an endoscope device of a second embodiment is cut along a plane perpendicular to the longitudinal axis.

Referring to FIG. 13, an endoscope device 11 of a second embodiment is described. The endoscope device 11 of the second embodiment differs from that of the first embodiment with respect to the position of the outer edge of the second rotary body 52, but the other parts are common to the first embodiment. Thus, different parts from the first embodiment will mainly be described, and illustrations or descriptions of parts common to the first embodiment is omitted.

The second rotary body 52 includes a second shaft portion 61 which is provided on the second surface 47 side and is rotatable relative to the case 45; and a second dial portion 62 which is fixed to a distal end portion of the second shaft portion 61. The second dial portion 62 has a columnar shape.

As illustrated in FIG. 13, in the present embodiment, that part 63A of the circular outer edge 63 of the second rotary body 52 (second dial portion 62), which is located on the distal-end direction 56A side of the first shaft portion 56, is located on the extension plane 64 which is defined by extending the first surface 46 of the operation main body 32 toward the periphery.

The operation of the endoscope device 11 of this embodiment is described. When the doctor bends the bending section 37 in one of the U direction and D direction (first direction) in the YZ plane, the doctor performs the same operation as in the first embodiment.

When the doctor wishes to bend the bending section 37 in one of the R direction and L direction in the XZ plane, the doctor rotates, as illustrated in FIG. 13, etc., the second dial portion 62 clockwise or counterclockwise by the inside of a finger other than the thumb (e.g. left middle finger). In the present embodiment, that part 63A of the outer edge 63 of the second rotary body 52, which is located on the distal-end direction 56A side of the first shaft portion 56, is located on the extension plane 64. Thus, when the second rotary body 52 is operated, the finger can be brought to the first surface 46 side. Thereby, the length, over which the finger (middle finger) is hooked on the outer edge 63 of the second rotary body 52, can be increased. Thus, the second rotary body 52 can be rotated over a large angle by a one-time operation.

The control device 13 operates the actuator unit 22 in accordance with the rotation amount of the second rotary body 52. Thereby, the bending section 37 bends in either the R direction or L direction.

According to the second embodiment, the introduction device includes the operation main body 32 provided with the first surface 46; the grip section 33 neighboring the operation main body 32 and provided along the longitudinal axis 35; the bending section 37 capable of bending in the first direction and the second direction crossing the first direction; the first rotary body 51 configured to be rotatable about the first shaft portion 56 projecting from the first surface 46, and to be operated at the time of bending the bending section 37 in the first direction; and the second rotary body 52 configured to be rotatable about the second shaft portion 61 projecting from the operation main body 32, and to be operated at the time of bending the bending section 37 in the second direction, the second rotary body 52 being configured such that the part 63A of the outer edge 63, which is located on the distal-end direction 56A side of the first shaft portion 56, is located on the extension plane 64 which is defined by extending the first surface 46.

According to this structure, the outer edge 63 of the second rotary body 52 can be disposed close to the first surface 46 side. Thereby, when the second rotary body 52 is operated, the finger can be brought to the first surface 46 side. Thus, when the second rotary body 52 is operated, the finger is prevented from abutting on the operation main body 32, and the length, over which the finger is hooked on the outer edge 63 of the second rotary body 52, can be increased.

Hence, the angle, over which the second rotary body 52 can be rotated by a one-time operation, can be increased, and the operability of the introduction device can be improved.

Third Embodiment

Referring to FIG. 14, an endoscope device 11 of a third embodiment is described. The endoscope device 11 of the third embodiment differs from that of the first embodiment with respect to the structure of the grip section 33 and the position of the outer edge 63 of the second rotary body 52, but the other parts are common to the first embodiment. Thus, different parts from the first embodiment will mainly be described, and illustrations or descriptions of parts common to the first embodiment is omitted.

FIG. 14 illustrates a cross section in which the grip section 33 is cut along a plane which is perpendicular to the longitudinal axis 35. As illustrated in FIG. 14, the grip section 33 has a substantially rectangular cross-sectional shape, with each corner portion being chamfered. The grip section 33 includes a pair of first holding surfaces 71 which are opposed to each other, a pair of second holding surfaces 72 which extend in a direction crossing the first holding surfaces 71, and chamfered portions 73 which are provided between the first holding surfaces 71 and second holding surfaces 72. The chamfered portion 73 (chamfered surface) is oblique to each of the first holding surface 71 and second holding surface 72. The chamfered portion 73, in the context of this invention, refers to a chamfered portion located between the first holding surface 71, which is located on the side where the first rotary body 51 is provided, and the second holding surface 72, which is located on the side where the second rotary body 52 is provided.

The second rotary body 52 includes a second shaft portion 61 which is provided on the second surface 47 side (second holding surface 72 side) and is rotatable relative to the case 45; and a second dial portion 62 which is fixed to a distal end portion of the second shaft portion 61. The second dial portion 62 has a columnar shape.

As illustrated in FIG. 14, in the present embodiment, that part 63A of the circular outer edge 63 of the second rotary body 52 (second dial portion 62), which is located on the distal-end direction 56A side of the first shaft portion 56, is located more on the distal-end direction 56A side of the first shaft portion 56 than an extension plane 64 which is defined by extending the chamfered portion 73 (chamfered surface). In addition, that part 63B of the outer edge 63 of the second rotary body 52 (second dial portion 62), which is located on the proximal-end direction 56B side of the first shaft portion 56, is located more on the proximal-end direction 56B side of the first shaft portion 56 than the extension plane 64.

The second shaft portion 61 of the second rotary body 52 is, in the direction of extension of the first shaft portion 56, provided more on the side (longitudinal axis 35 side) where the operation main body 32 is located, than the extension plane 64. In addition, the second rotary body 52 is disposed in the same positional relationship as in the endoscope device 11 shown in FIG. 5. Specifically, in this embodiment, the second shaft portion 61, as viewed from the first surface 46 side, is located between the longitudinal axis 35 and the tangent 65B which is located on the side opposite to the side where the first rotary body 51 is operated by the thumb.

The operation of the endoscope device 11 of this embodiment is described. When the doctor bends the bending section 37 in one of the U direction and D direction (first direction) in the YZ plane, the doctor performs the same operation as in the first embodiment.

When the doctor wishes to bend the bending section 37 in one of the R direction and L direction in the XZ plane, the doctor rotates, as illustrated in FIG. 14, etc., the second dial portion 62 clockwise or counterclockwise by the inside of a finger other than the thumb (e.g. left middle finger). In the present embodiment, that part 63A of the outer edge 63 of the second rotary body 52, which is located on the distal-end direction 56A side of the first shaft portion 56, is located more on the distal-end direction 56A side of the first shaft portion 56 than the extension plane 64. Thus, when the second rotary body 52 is operated, the finger can be brought to the chamfered portion 73 side. Thereby, the length, over which the finger (middle finger) is hooked on the outer edge of the second rotary body 52, can be increased. Thus, the second rotary body 52 can be rotated over a large angle by a one-time operation.

The control device 13 operates the actuator unit 22 in accordance with the rotation amount of the second rotary body 52. Thereby, the bending section 37 bends in either the R direction or L direction.

According to the third embodiment, the introduction device includes the operation main body 32; the bending section 37 capable of bending in the first direction and the second direction crossing the first direction; the first rotary body 51 configured to be rotatable about the first shaft portion 56 projecting from the operation main body 32, and to be operated at the time of bending the bending section 37 in the first direction; the grip section 33 including the first holding surface 71 located on the side where the first rotary body 51 is provided, the second holding surface 72 neighboring the first holding surface 71, and the chamfered portion 73 located between the first holding surface 71 and the second holding surface 72, the grip section 33 neighboring the operation main body 32 and being provided along the longitudinal axis 35; and the second rotary body 52 provided on the second holding surface 72 side in a manner to be rotatable about the second shaft portion 61 projecting from the operation main body 32, and configured to be operated at the time of bending the bending section 37 in the second direction, the second rotary body 52 being configured such that the part 63A of the outer edge 63, which is located on the distal-end direction 56A side of the first shaft portion 56, is located more on the distal-end direction 56A side of the first shaft portion 56 than the extension plane 64, and configured such that the part 63B of the outer edge 63, which is located on the proximal-end direction 56B side of the first shaft portion 56, is located more on the proximal-end direction 56B side of the first shaft portion 56 than the extension plane 64.

According to this structure, the outer edge 63 of the second rotary body 52 can be disposed to project to the distal-end direction 56A side of the first shaft portion 56, in relation to the grip section 33. Thereby, when the second rotary body 52 is operated, the finger can be brought to the chamfered portion 73 side. Thus, the length, over which the finger is hooked on the outer edge 63 of the second rotary body 52, can be increased, and the second rotary body 52 can be rotated over a large angle by a one-time operation. Hence, the operability of the introduction device can be improved.

Fourth Embodiment

Referring to FIG. 15, an endoscope device of a fourth embodiment is described. The endoscope device 11 of the fourth embodiment differs from that of the third embodiment with respect to the position of the outer edge 63 of the second rotary body 52, but the other parts are common to the third embodiment. Thus, different parts from the third embodiment will mainly be described, and illustrations or descriptions of parts common to the third embodiment is omitted.

FIG. 15 illustrates a cross section in which the grip section 33 is cut along a plane which is perpendicular to the longitudinal axis 35. As illustrated in FIG. 15, the grip section 33 has a substantially rectangular cross-sectional shape, with each corner portion being chamfered. The grip section 33 includes a pair of first holding surfaces 71 which are opposed to each other, a pair of second holding surfaces 72 which extend in a direction crossing the first holding surfaces 71, and chamfered portions 73 which are provided between the first holding surfaces 71 and second holding surfaces 72. The chamfered portion 73, in the context of this invention, refers to a chamfered portion located between the first holding surface 71, which is located on the side where the first rotary body 51 is provided, and the second holding surface 72, which is located on the side where the second rotary body 52 is provided.

The second rotary body 52 includes a second shaft portion 61 which is provided on the second surface 47 side (second holding surface 72 side) and is rotatable relative to the case 45; and a second dial portion 62 which is fixed to a distal end portion of the second shaft portion 61.

As illustrated in FIG. 15, in the present embodiment, that part 63A of the circular outer edge 63 of the second rotary body 52 (second dial portion 62), which is located on the distal-end direction 56A side of the first shaft portion 56, is located on the extension plane 64 which is defined by extending the chamfered portion 73 (chamfered surface).

The second shaft portion 61 of the second rotary body 52 is, in the direction of extension of the first shaft portion 56, provided more on the side (longitudinal axis 35 side) where the operation main body 32 is located, than the extension plane 64. In addition, the second rotary body 52 is disposed in the same positional relationship as in the endoscope device 11 shown in FIG. 5. The second shaft portion 61, as viewed from the first surface 46 side, is located between the longitudinal axis 35 and the tangent 65B which is located on the side opposite to the side where the first rotary body 51 is operated by the thumb.

The operation of the endoscope device 11 of this embodiment is described. When the doctor bends the bending section 37 in one of the U direction and D direction (first direction) in the YZ plane, the doctor performs the same operation as in the first embodiment.

When the doctor wishes to bend the bending section 37 in one of the R direction and L direction in the XZ plane, the doctor rotates, as illustrated in FIG. 15, etc., the second dial portion 62 clockwise or counterclockwise by the inside of a finger other than the thumb (e.g. left middle finger). In the present embodiment, that part 63A of the outer edge 63 of the second rotary body 52, which is located on the distal-end direction 56A side of the first shaft portion 56, is located on the extension plane 64. Thus, when the second rotary body 52 is operated, the finger can be brought to the chamfered portion 73 side. Thereby, the length, over which the finger (middle finger) is hooked on the outer edge 63 of the second rotary body 52, can be increased. Thus, the second rotary body 52 can be rotated over a large angle by a one-time operation.

The control device 13 operates the actuator unit 22 in accordance with the rotation amount of the second rotary body 52. Thereby, the bending section 37 bends in either the R direction or L direction.

According to the present embodiment, the introduction device includes the operation main body 32; the bending section 37 capable of bending in the first direction and the second direction crossing the first direction; the first rotary body 51 configured to be rotatable about the first shaft portion 56 projecting from the operation main body 32, and to be operated at the time of bending the bending section 37 in the first direction; the grip section 33 including the first holding surface 71 located on the side where the first rotary body 51 is provided, the second holding surface 72 neighboring the first holding surface 71, and the chamfered portion 73 located between the first holding surface 71 and the second holding surface 72, the grip section 33 neighboring the operation main body 32 and being provided along the longitudinal axis 35; and the second rotary body 52 provided on the second holding surface 72 side in a manner to be rotatable about the second shaft portion 61 projecting from the operation main body 32, and configured to be operated at the time of bending the bending section 37 in the second direction, the second rotary body 52 being configured such that the part 63A of the outer edge 63, which is located on the distal-end direction 56A side of the first shaft portion 56, is located on the extension plane 64 which is defined by extending the chamfered portion 73.

According to this structure, the outer edge 63 of the second rotary body 52 can be disposed close to the chamfered portion 73 side of the grip section 33. Thereby, the finger can be brought to the chamfered portion 73 side, while the finger is prevented from abutting on the operation main body 32. Hence, the length, over which the finger is hooked on the outer edge 63 of the second rotary body 52, can be increased, and the second rotary body 52 can be rotated over a large angle by a one-time operation. Therefore, the operability of the introduction device can be improved.

Fifth Embodiment

Figure 16:
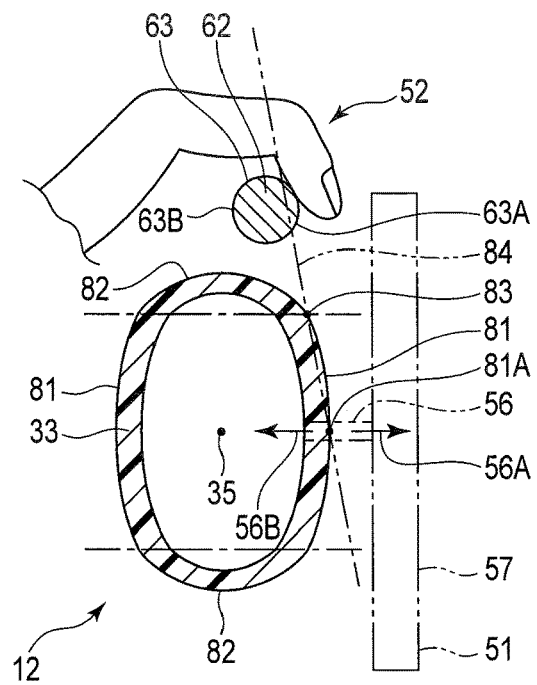
FIG. 16 is a cross-sectional view illustrating the position of the second rotary body, FIG. 16 being a cross-sectional view in which an endoscope of an endoscope device of a fifth embodiment is cut along a plane perpendicular to the longitudinal axis.

Referring to FIG. 16, an endoscope device 11 of a fifth embodiment is described. The endoscope device 11 of the fifth embodiment differs from that of the first embodiment with respect to the structure of the grip section 33 and the position of the outer edge 63 of the second rotary body 52, but the other parts are common to the first embodiment. Thus, different parts from the first embodiment will mainly be described, and illustrations or descriptions of parts common to the first embodiment is omitted.

FIG. 16 illustrates a cross section in which the grip section 33 is cut along a plane which is perpendicular to the longitudinal axis 35. As illustrated in FIG. 16, the grip section 33 has a cross-sectional shape (substantially elliptic shape) in which two pairs of surfaces with different curvatures (radii of curvature) are combined. The grip section 33 includes a pair of first curved surfaces 81 which are opposed to each other, a pair of second curved surfaces 82 which extend in a direction crossing the first curved surfaces 81, and a boundary portion 83 provided between the first curved surface 81 and second curved surface 82. In this embodiment, a boundary located between the first curved surface 81, which is located on the side where the first rotary body 51 is provided, and the second curved surface 82 located on the side where the second rotary body 52 is provided, is referred to as the boundary portion 83. The boundary portion 83 is disposed linearly along the longitudinal axis 35, and divides the first curved surface 81 and second curved surface 82.

The first curved surface 81, which is located on the side where the first rotary body 51 is provided, includes an apex portion 81A. The apex portion 81A constitutes that portion of the first curved surface 81, which is most projecting to the distal-end direction 56A side of the first shaft portion 56.

The second rotary body 52 includes a second shaft portion 61 which is provided on the second surface 47 side (second curved surface 82 side) and is rotatable relative to the case 45; and a second dial portion 62 which is fixed to a distal end portion of the second shaft portion 61. The second dial portion 62 has a columnar shape.

As illustrated in FIG. 16, in the present embodiment, that part 63A of the circular outer edge 63 of the second rotary body 52 (second dial portion 62), which is located on the distal-end direction 56A side of the first shaft portion 56, is located more on the distal-end direction 56A side of the first shaft portion 56 than a plane 84 including the boundary portion 83 and apex portion 81A. In addition, that part 63B of the outer edge 63 of the second rotary body 52 (second dial portion 62), which is located on the proximal-end direction 56B side of the first shaft portion 56, is located more on the proximal-end direction 56B side of the first shaft portion 56 than the plane 84.

The second shaft portion 61 of the second rotary body 52 is, in the direction of extension of the first shaft portion 56, provided more on the side (longitudinal axis 35 side) where the operation main body 32 is located, than the plane 84. In addition, the second rotary body 52 is disposed in the same positional relationship as in the endoscope device 11 shown in FIG. 5. Specifically, in this embodiment, the second shaft portion 61, as viewed from the first surface 46 side, is located between the longitudinal axis 35 and the tangent 65B which is located on the side opposite to the side where the first rotary body 51 is operated by the thumb.

The operation of the endoscope device 11 of this embodiment is described. When the doctor bends the bending section 37 in one of the U direction and D direction (first direction) in the YZ plane, the doctor performs the same operation as in the first embodiment.

When the doctor wishes to bend the bending section 37 in one of the R direction and L direction in the XZ plane, the doctor rotates, as illustrated in FIG. 16, etc., the second dial portion 62 clockwise or counterclockwise by the inside of a finger other than the thumb (e.g. left middle finger). In the present embodiment, that part 63A of the outer edge 63 of the second rotary body 52, which is located on the distal-end direction 56A side of the first shaft portion 56, is located more on the distal-end direction 56A side of the first shaft portion 56 than the plane 84. Thus, when the second rotary body 52 is operated, the finger can be brought to the first curved surface 81 side. Thereby, the length, over which the finger (middle finger) is hooked on the outer edge 63 of the second rotary body 52, can be increased. Thus, the second rotary body 52 can be rotated over a large angle by a one-time operation.

The control device 13 operates the actuator unit 22 in accordance with the rotation amount of the second rotary body 52. Thereby, the bending section 37 bends in either the R direction or L direction.

According to the fifth embodiment, the introduction device includes the operation main body 32; the bending section 37 capable of bending in the first direction and the second direction crossing the first direction; the first rotary body 51 configured to be rotatable about the first shaft portion 56 projecting from the operation main body 32, and to be operated at the time of bending the bending section 37 in the first direction; the grip section 33 including the first curved surface 81 including the apex portion 81A located on the distal-end direction 56A side of the first shaft portion 56, and the second curved surface 82 extending in a direction crossing the first curved surface 81, the grip section 33 neighboring the operation main body 32 and including the longitudinal axis 35; and the second rotary body 52 provided on the second curved surface 82 side in a manner to be rotatable about the second shaft portion 61 projecting from the operation main body 32, and configured to be operated at the time of bending the bending section 37 in the second direction, the second rotary body 52 being configured such that the part 63A of the outer edge 63, which is located on the distal-end direction 56A side of the first shaft portion 56, is located more on the distal-end direction 56A side of the first shaft portion 56 than the plane 84 including the boundary portion 83 and the apex portion 81A, and configured such that the part 63B of the outer edge 63, which is located on the proximal-end direction 56B side of the first shaft portion 56, is located more on the proximal-end direction 56B side of the first shaft portion 56 than the plane 84.

According to this structure, the outer edge 63 of the second rotary body 52 can be disposed to project to the distal-end direction 56A side of the first shaft portion 56, in relation to the grip section 33. Thereby, when the second rotary body 52 is operated, the finger can be brought to the first curved surface 81 side. Thus, the length, over which the finger is hooked on the outer edge 63 of the second rotary body 52, can be increased, and the second rotary body 52 can be rotated over a large angle by a one-time operation. Hence, the operability of the introduction device can be improved.

Sixth Embodiment

Figure 17:
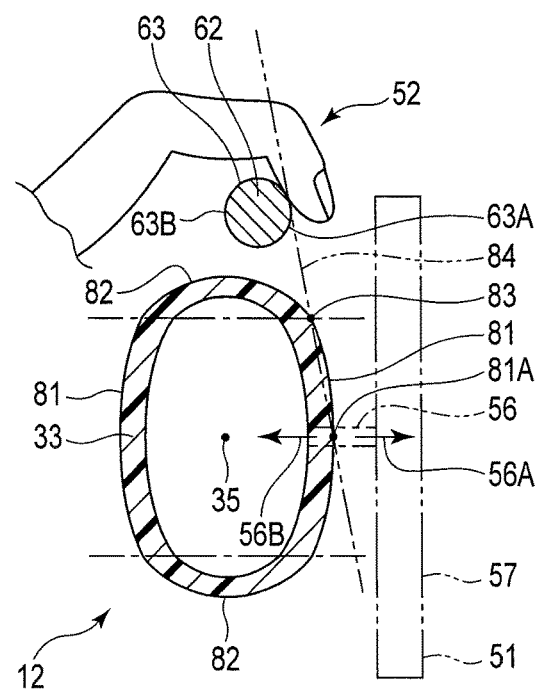
FIG. 17 is a cross-sectional view illustrating the position of the second rotary body, FIG. 17 being a cross-sectional view in which an endoscope of an endoscope device of a sixth embodiment is cut along a plane perpendicular to the longitudinal axis.

Referring to FIG. 17, an endoscope device 11 of a sixth embodiment is described. The endoscope device 11 of the sixth embodiment differs from that of the fifth embodiment with respect to the position of the outer edge 63 of the second rotary body 52, but the other parts are common to the fifth embodiment. Thus, different parts from the fifth embodiment will mainly be described, and illustrations or descriptions of parts common to the fifth embodiment is omitted.

FIG. 17 illustrates a cross section in which the grip section 33 is cut along a plane which is perpendicular to the longitudinal axis 35. As illustrated in FIG. 17, the grip section 33 has a cross-sectional shape in which two pairs of surfaces with different curvatures (radii of curvature) are combined. The grip section 33 includes a pair of first curved surfaces 81 which are opposed to each other, a pair of second curved surfaces 82 which extend in a direction crossing the first curved surfaces 81, and a boundary portion 83 provided between the first curved surface 81 and second curved surface 82. In this embodiment, a boundary located between the first curved surface 81, which is located on the side where the first rotary body 51 is provided, and the second curved surface 82 located on the side where the second rotary body 52 is provided, is referred to as the boundary portion 83. The boundary portion 83 is disposed linearly along the longitudinal axis 35, and divides the first curved surface 81 and second curved surface 82.

The second rotary body 52 includes a second shaft portion 61 which is provided on the second surface 47 side and is rotatable relative to the case 45; and a second dial portion 62 which is fixed to a distal end portion of the second shaft portion 61. The second dial portion 62 has a columnar shape.

As illustrated in FIG. 17, in the present embodiment, that part 63A of the circular outer edge 63 of the second rotary body 52 (second dial portion 62), which is located on the distal-end direction 56A side of the first shaft portion 56, is located on the plane 84 including the boundary portion 83 and apex portion 81A.

The second shaft portion 61 of the second rotary body 52 is, in the direction of extension of the first shaft portion 56, provided more on the side (longitudinal axis 35 side) where the operation main body 32 is located, than the plane 84. In addition, the second rotary body 52 is disposed in the same positional relationship as in the endoscope device 11 shown in FIG. 5. Specifically, in this embodiment, the second shaft portion 61, as viewed from the first surface 46 side, is located between the longitudinal axis 35 and the tangent 65B which is located on the side opposite to the side where the first rotary body 51 is operated by the thumb.

The operation of the endoscope device 11 of this embodiment is described. When the doctor bends the bending section 37 in one of the U direction and D direction (first direction) in the YZ plane, the doctor performs the same operation as in the first embodiment.

When the doctor wishes to bend the bending section 37 in one of the R direction and L direction in the XZ plane, the doctor rotates, as illustrated in FIG. 17, etc., the second dial portion 62 clockwise or counterclockwise by the inside of a finger other than the thumb (e.g. left middle finger). In the present embodiment, that part of the outer edge 63 of the second rotary body 52, which is located on the distal-end direction 56A side of the first shaft portion 56, is located on the plane 84. Thus, when the second rotary body 52 is operated, the finger can be brought to the first curved surface 81 side. Thereby, the length, over which the finger (middle finger) is hooked on the outer edge 63 of the second rotary body 52, can be increased. Thus, the second rotary body 52 can be rotated over a large angle by a one-time operation.

The control device 13 operates the actuator unit 22 in accordance with the rotation amount of the second rotary body 52. Thereby, the bending section 37 bends in either the R direction or L direction.

According to the present embodiment, the introduction device includes the operation main body 32; the bending section 37 capable of bending in the first direction and the second direction crossing the first direction; the first rotary body 51 configured to be rotatable about the first shaft portion 56 projecting from the operation main body 32, and to be operated at the time of bending the bending section 37 in the first direction; the grip section 33 including the first curved surface 81 including the apex portion 81A located on the distal-end direction 56A side of the first shaft portion 56, and the second curved surface 82 extending in a direction crossing the first curved surface 81, the grip section 33 neighboring the operation main body 32 and including the longitudinal axis 35; and the second rotary body 52 provided on the second curved surface 82 side in a manner to be rotatable about the second shaft portion 61 projecting from the operation main body 32, and configured to be operated at the time of bending the bending section 37 in the second direction, the second rotary body 52 being configured such that the part 63A of the outer edge 63, which is located on the distal-end direction 56A side of the first shaft portion 56, is located on the plane including the boundary portion 83, which forms the boundary between the first curved surface 81 and second curved surface 82, and the apex portion 81A.

According to this structure, the outer edge 63 of the second rotary body 52 can be disposed close to the first curved surface 81 of the grip section 33. Thereby, when the second rotary body 52 is operated, the finger can be brought to the first curved surface 81 side. Thus, the length, over which the finger is hooked on the outer edge 63 of the second rotary body 52, can be increased, and the second rotary body 52 can be rotated over a large angle by a one-time operation. Hence, the operability of the introduction device can be improved.

The present invention is not limited to the above-described embodiments, and modifications may be implemented where necessary, without departing from the spirit of the invention. For example, as a modification of each of the above-described embodiments, as illustrated in FIG. 18, the bending section 37 may be composed of multiple stages, and the operation of the second dial portion 62 may be assigned thereto. In a mode of the multiple-stage configuration, it is thinkable that a first bending section 37A is provided on the distal end side of the insertion section 34, and a second bending section 37B is provided on the proximal end side of the first bending section 37A. In this case, at least the first wires 41 are coupled to the first bending section 37A. If the first rotary body 51 is rotated by the finger, etc., the first bending section 37A is bent in the first direction (U direction or D direction). Furthermore, a pair of wires are also coupled to the second bending section 37B, and the second bending section 37B is bent in the second direction (U direction or D direction) by pulling the paired wires by the driving force of the actuator unit 22. Specifically, in this modification, the second direction is a direction along the first direction (a direction parallel to the first direction). The actuator unit 22 is controlled based on the rotational direction and rotation amount of the second dial portion 62, which are detected by the rotation detection sensor 49. In addition, one endoscope device may be composed by combining the endoscope devices of the above-described embodiments.

In each of the above-described embodiments, the endoscope is used as an example of the introduction device. Other examples of the introduction device include an introduction device which does not include the illumination optical system including the light source device 14 and illumination lenses 24 of the distal rigid section 23, or the observation optical system including the image capturing device 15, monitor 21 and the objective lens 26 of the distal rigid section 23.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

11 . . . Endoscope device, 12 . . . Endoscope, 32 . . . Operation main body, 33 . . . Grip section, 35 . . . Longitudinal axis, 37 . . . Bending section, 46 . . . First surface, 51 . . . First rotary body, 52 . . . Second rotary body, 56 . . . First shaft portion, 56A . . . Distal-end direction, 56B . . . Proximal-end direction, 61 . . . Second shaft portion, 63 . . . Outer edge, 63A . . . Part, 63B . . . Part, 64 . . . Extension surface, 65B . . . Other tangent, 71 . . . First holding surface 72 . . . Second holding surface, 73 . . . Chamfered portion, 81 . . . First curved surface, 81A . . . Apex portion, 82 . . . Second curved surface, 83 . . . Boundary portion, 84 . . . Plane.

What is claimed is:

1. An introduction device comprising:
a bending section capable of bending in a first direction and a second direction that intersects with the first direction;
an operation main body configured to be gripped by a user when bending the bending section;
a first rotary body configured to be rotatable about a first shaft portion, a distal-end portion of the first shaft portion projecting from the operation main body, and to be operated to bend the bending section in the first direction;
a grip section provided adjacent to the operation main body including a first curved surface including an apex portion projecting most to a distal-end direction side of the first shaft portion, and a second curved surface extending in a direction crossing the first curved surface and having a curvature different from that of the first curved surface; and
a second rotary body provided on the second curved surface side in a manner to be rotatable about a second shaft portion projecting from the operation main body, and configured to be operated to bend the bending section in the second direction, the second rotary body being configured such that a part of an outer edge of the second rotary body, which part is located on the distal-end direction side of the first shaft portion, is located on a plane including the apex portion and a boundary portion which forms a boundary between the first curved surface and the second curved surface when viewing the grip section along a cross-sectional plane which intersects with a longitudinal axis of the grip section, on the cross-sectional plane, the boundary portion corresponds to a nondifferentiable point between a first curved line corresponding to the first curved surface and a second curved line corresponding to the second curved surface.

2. The introduction device of claim 1, wherein the second rotary body is provided to be exposed from the operation main body.

3. The introduction device of claim 2, wherein the operation main body has a first surface on which the first rotary body is provided, and the second shaft portion is, in the direction of extension of the first shaft portion, located more on a side where the operation main body is located, than the extension plane that is an extension of the first surface.

4. The introduction device of claim 3, wherein, as viewed from the first surface side, a portion of the second shaft portion is included within a range of a circumscribed circle of the first rotary body, and the second shaft portion is located between a longitudinal axis and a tangent which is located on a side opposite to a side where the first rotary body is operated by a thumb, the tangent being one of tangents of the circumscribed circle, which are parallel to the longitudinal axis.

* * * * *